(12) United States Patent
Bolz

(10) Patent No.: US 6,463,325 B1
(45) Date of Patent: Oct. 8, 2002

(54) SELF-CALIBRATING RATE-ADAPTIVE CARDIAC PACEMAKER

(75) Inventor: Armin Bolz, Weingarten (DE)

(73) Assignee: Biotronki Mess-und Therapeigerate GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/464,674

(22) Filed: Dec. 15, 1999

(30) Foreign Application Priority Data

Dec. 15, 1998 (DE) .................................. 198 59 653

(51) Int. Cl.$^7$ .................................. A61N 0/18
(52) U.S. Cl. .................................. 607/18
(58) Field of Search .................. 607/4, 5, 9, 18, 607/17, 25, 27

(56) References Cited

U.S. PATENT DOCUMENTS

| | | | |
|---|---|---|---|
| 4,867,160 A | 9/1989 | Schaldach | 128/419 |
| 5,065,759 A | * 11/1991 | Begemann et al. | 128/419 |
| 5,111,815 A | 5/1992 | Mower | 128/419 |
| 5,154,171 A | * 10/1992 | Chirife | 128/419 |
| 5,441,525 A | 8/1995 | Shelton et al. | 607/23 |
| 5,487,753 A | 1/1996 | MacCarter et al. | 607/17 |
| 5,645,570 A | 7/1997 | Corbucci | 607/5 |
| 5,749,900 A | * 5/1998 | Schroeppel et al. | 607/4 |

FOREIGN PATENT DOCUMENTS

| | | |
|---|---|---|
| DE | 44 47 447 | 7/1996 |
| DE | 196 09 382 | 9/1997 |
| DE | 196 54 494 | 5/1998 |
| DE | 198 04 843 | 8/1999 |
| EP | 0 147 820 | 7/1985 |
| EP | 0 498 533 | 8/1992 |
| EP | 0 565 909 | 10/1993 |
| EP | 0 793 976 | 9/1997 |
| EP | 0 804 938 | 11/1997 |
| WO | WO 92/04076 | 3/1992 |
| WO | WO 93/20889 | 10/1993 |
| WO | WO 96/35476 | 11/1996 |
| WO | WO 97/36637 | 10/1997 |

OTHER PUBLICATIONS

M. Schaldach, "Electrotherapy of the Heart"; Springer–Verlag, 1992, Foreward, pp. 114–121.
M. Schaldach, "PEP–gesteuerter Herzschrittmacher" Pacemaker with PEP–Controlled Rate Adaptation; Biomed. Technik, 34 (1989) pp. 177–184.
A. Urbaszek, "Intrakardiale Impedanzmessung zur Bestimmung der Sympathikusaktivitat bei frequenzadaptiver Electrostimulation—Teil 1: Biomedizintechnische Grundlagen" Biomedizinische Technik, 37, 1992, pp. 155–161.
A. M. Pichlmaier et al., "Intrakardiale Impedanzmessung zur Bestimmung der Sympathikusaktivitat bei frequenzadaptiver Elektrostimulation—Teil 2: Klinische Ergebnisse", Biomed Technik 37, 1992, pp. 188–193.

* cited by examiner

*Primary Examiner*—George R. Evanisko
*Assistant Examiner*—Frances P. Oropeza
(74) *Attorney, Agent, or Firm*—Christie, Parker & Hale, LLP

(57) ABSTRACT

A self-calibrating rate-adaptive cardiac pacemaker is provided. The pacemaker comprising a first measuring and processing device for detecting a first, predominantly sympathetically influenced physiological parameter and for obtaining a rate control parameter, which has a control input for controlling the functional dependency of the rate control parameter on the first physiological parameter, in particular a response factor and/or an upper limit rate; and a stimulator unit for producing and outputting stimulation pulses at a stimulation rate which is determined by the rate control parameter, having a second measuring and processing device for detecting and evaluating a second, predominantly vagally influenced physiological parameter and for outputting a calibration signal which is dependent on the evaluation result, to the control input of the first measuring and processing device.

10 Claims, 1 Drawing Sheet

SELF-CALIBRATING RATE-ADAPTIVE CARDIAC PACEMAKER

FIELD OF THE INVENTION

The invention concerns a cardiac pacemaker and more particularly to a self-calibrating rate-adaptive cardiac pacemaker.

BACKGROUND OF INVENTION

Rate-adaptive cardiac pacemakers wherein the stimulation rate is set in dependence on signals received from the body of the patient, and which reflect the physiological demand of the patient with regard to cardiac activity, have long been known and used in a clinical context. Various proposals have also been put forward for self-adaptation (auto-calibration) of such rate-adaptive cardiac pacemakers.

For example, WO 93/20889 proposes a dual-sensor arrangement with one circuit for detecting the minute volume, and an additional activity sensor where the stimulation rate is determined based on target rates, which can be derived for the individual sensors. In another example, U.S. Pat. No. 5,065,759 proposes a dual-sensor arrangement in which the QT-interval is detected and evaluated as a, 'physiologically exact', but slowly responding parameter, and wherein physical activity is detected and evaluated as a rapidly responding parameter.

In yet another example, EP 0 147 820 also discloses a rate-adaptive pacemaker in which one of the two sensors is used as a so-called closed-loop sensor, which detects signals from the heart-circulation regulating circuit for rate adaptation purposes, whereas a further sensor only provides a monitoring function. In this system, it is only when errors in rate adaptation are detected by way of the monitoring sensor that the closed-loop sensor is temporarily replaced by the monitoring sensor or the configuration of the sensor characteristic is re-calibrated.

Meanwhile, EP 0 498 533 A1 proposes a rate-adaptive pacemaker operating with two sensors, in which the upper rate limit is set utilizing hemodynamical monitoring. Various sensors are known for this function, including a sensor designed to detect changes in the impedance of the right ventricle.

Finally, in an unpublished German patent application No. P 198 04 843.2, a self-calibrating rate-adaptive pacemaker was proposed in which a closed-loop rate adaptation algorithm based on intraventricularly detected impedance signals was calibrated by means of an acceleration sensor.

Signals emanating from the sympathetic nerve in the context of the autonomous system for heart-circulation control, referred to as 'sympathetic' signals, primarily indicate the need for cardiac minute volume, and in the neural equilibrium of the sound heart-circulation system, find their antagonist in signals emanating from the vagus nerve, referred to as 'vagal' or 'parasympathetic' signals, which indicate the attainment of upper limits in terms of the efficiency of the cardiac minute volume. In contrast to sympathetic signals, vagal signals therefore have an inhibiting effect.

In the known rate-adaptive pacemakers the change in inotropy is measured and used as a measurement of the required cardiac minute volume, and thus the optimum stimulation rate. In this respect, a linear relationship is assumed between inotropy and heart rate, i.e., a rise in inotropy is immediately answered by a proportional rise in the stimulation rate. Measurement of the inotropy by way of the ventricular contraction dynamics (by means of unipolar impedance measurement) predominantly detects the sympathetic component of autonomous regulation. Vagal components, and their (generally inhibiting) effect on the heart rate, are in practice not detected and taken into consideration. This 'purely sympathetic' pacemaker consequently functions—at least in relation to heart rate—in an analogous fashion to a patient with a low level of baroreceptor reflex sensitivity; the vagal tone is artificially reduced to zero or set to a constant value and the sympathetic tone alone has a controlling action. This sympathetic dominant system results in two disadvantages: 1) rapid heart rate adaptations, as are possible with vagal involvement in relation to the functioning heart, cannot be implemented by the pacemaker; and 2) the function of the vagus nerve for controlling the heart rate dynamics also does not have any effect. This means that long-term effects (for example general physical fatigue—so-called 'burn-out'—, a harbinger of incipient heart insufficiency, etc.) remain substantially disregarded.

This means that the actual advantage of autonomous monitoring, namely sparing the inotropic reserves and thus protecting against primary cardiomyopathies or arrhythmias, are not utilized in an optimal fashion. As a consequence of disregarding the vagal contribution, the calculated stimulation rate is not physiologically correct in terms of its absolute level, even if fall and rise times may be correct. The result is that the myocardium may, under some circumstances, be overloaded or not adequately loaded.

Accordingly, a need exists for a cardiac pacemaker of the general kind set forth above, which is optimized from the physiological point of view, which operates in a reliably self-calibrating fashion, and which can be implemented without problems.

SUMMARY OF THE INVENTION

The present invention is directed to a self-calibrating rate-adaptive cardiac pacemaker, and more particularly to a self-calibrating rate-adaptive cardiac pacemaker comprising a first measuring and processing device for detecting a first, predominantly sympathetically influenced physiological parameter ($Z(tm)$) and for obtaining a rate control parameter (RCPp), which has a control input for controlling the functional dependency of the rate control parameter on the first physiological parameter, in particular a response factor and/or an upper limit rate; and a stimulator unit for producing and outputting stimulation pulses at a stimulation rate which is determined by the rate control parameter, characterized by a second measuring and processing device for detecting and evaluating a second, predominantly vagally influenced physiological parameter (AVI) and for outputting a calibration signal (Cal) which is dependent on the evaluation result, to the control input of the first measuring and processing device.

In one embodiment, the invention is directed to a pacemaker which operates with a suitable vagal control contribution, and which uses signals from two closed-loop sensors for rate control purposes and more specifically a sensor which hereinafter is referred to for the sake of brevity as the 'sympathetic' sensor and a sensor which is referred to as the 'vagal' sensor. The influence of the vagus is primarily felt in the electrical and mechanical activity of the atria, such as, for example, the atrial evoked stimulation response {AER—to be measured by a unipolar procedure), the atrial monophase action potential {MAP—to be measured by a bipolar procedure), the atrial refractory time, the intra-atrial impedance, and also the AV-transition time. Meanwhile, the influence of the sympathetic nerve is expressed primarily in the activity of the ventricle, and more particularly to the ventricularly evoked stimulation response {VER), the ventricular monophase action potential {MAP), the ventricular refractory time, the intra-ventricular impedance, and the QT-interval. In such an embodiment, the sensor for signals which are dominated by the sympathetic nerve is referred to as the 'sympathetic' sensor, and the sensor for signals dominated by the vagus nerve is referred to as the 'vagal' sensor. In such a system the sympathetic signals react to changes in the heart-circulation system more slowly (with a time constant of about cardiac cycles) than vagal signals (with a time constant of about one cardiac cycle) and therefore the sensor time characteristics are also correspondingly different.

In one alternative embodiment, the invention includes the ability to current control the stimulation frequency in a closed-loop stimulation (CLS) with reference to the signals from the 'sympathetic' sensor.

In another alternative embodiment, the relative changes in the sensor signal are converted, in accordance with the response amplification effect or the response factor (which represents a measurement of the sensor dynamics), into stimulation frequencies which are directly proportional thereto, or, alternatively, into absolute sensor values are converted by way of a characteristic curve into rate-control signals.

In yet another alternative embodiment, the vagal sensor is used for calibration of the sympathetic sensor or more particularly the sensor dynamics (response factor or rise in the sensor characteristic) and the rate range which can be covered in the current control situation. For example, if the rate adaptation algorithm, by means of the sympathetic sensor, provides for ascertaining stimulation rates which are dynamically excessive or which basically are above the efficiency of the heart-circulation system, i.e., outside the hemodynamically justified rate range; then the inhibiting influence of the vagal nervous system is utilized through the vagal sensor. If, on the other hand, the vagus tone is low, the response factor and upper limit rate are increased and the sympathetic nerve tone reduced, whereupon a rise in vagus tone is to be expected.

In still another embodiment of the invention, (irrespective of the above-mentioned assumption of the fundamental dominance of sympathetic or vagal components in given kinds of cardiac signals), the separation of sympathetic and vagal signal components in the available, complexly determined signals is of particular significance. In such an embodiment, one possible way of separating the vagal and sympathetic signals, which is advantageous in terms of measuring procedure and which is very close to the behaviour of a healthy heart-circulation system, is based on modulation of the two tones and analysis of the responses of a suitably selected effector utilizing the different time constants. Therefore, the stimulation rate is modulated around the adaptive rate. Rapid modulation of the stimulation frequency (specifically on a beat-to-beat basis) can produce a variation, which is also rapid, in the signals of the vagal sensor, which variation must in turn assume a given extent in the optimum efficiency range of the heart. In contrast, slow modulation (extending for example over 10 cardiac cycles) of the stimulation frequency entrains a variation in the sympathetic signals.

In still yet another embodiment, the invention uses the intra-ventricular impedance as the sympathetic signal for rate adaptation purposes and the natural AV-transition time as the vagal signal for calibration purposes. In such an embodiment, detecting and suitably evaluating the intra-ventricular impedance allows for the measurement of the inotropy (beat strength or force of the cardiac muscle) and calculating therefrom the stimulation rate. In such a case excessive stimulation rates may occur with a rising stress and an excessive response factor. The AV-transition time— which is basically reduced in length with physiologically appropriately rising rate values—reacts thereto with an unnatural increase in length. Conversely, the AV-transition time reacts to a rise in the stimulation frequency, which is too low in relation to the hemodynamic demand, with an unnatural reduction in length. If the above-mentioned unnatural behaviour in terms of the AV-transition time is detected, the response factor can be corrected. On the basis of such a calibration, it is possible for the upper MCLR limit ('maximum closed-loop rate') for the sensor rate range to be dynamically established as, when the maximum physiological stimulation rate is exceeded, the above- described unnatural increase in length of the AV-transition time may be noted.

In still yet another embodiment, calibration both in respect of sensor dynamics and also the sensor rate range can be implemented on the basis of the modulation of the stimulation frequency. In such an embodiment, in the case of rapid modulation, the variation in the AV-time at excessive stimulation rates, in comparison with its variation in the case of physiological stimulation rates, is displaced towards longer AV-times. This applies both with respect to instantaneously excessive stimulation rates and also stimulation rates which are above the efficiency of the heart.

In still yet another embodiment, evaluation of the impedance measurements is effected in accordance with the known ResQ- or rise processes (SCHALDACH, Max: Electrotherapy of the Heart, 1st edition, Springer-Verlag, pages 114 ff) in a wide range, which includes the ROI-ranges which are usually set for individual patients. In such an embodiment, the sensing time pairs are pre-programmed in such a way that they contain the pair which is 'optimum' for the patient in question. Establishing this optimum pair does not require programming individually to the patient after the implantation procedure. Instead, such values are preferably stored in a read-only memory during the production of the pacemaker. In such an embodiment, impedance detection and evaluation can be effected at a spontaneous ventricular signal, but by virtue of the signal shape which in such a situation is often unfavourable and fluctuating, detection at an evoked signal (VER) is preferred in practice. The point of reference for the choice of the sensing time pair in such a case is the ventricular stimulus.

In still yet another embodiment, the invention is directed to a process capable of managing the cardiac pacemaker with a lower level of calibration. In such an embodiment, the process calculates a value of the integral of the impedance curve on the basis of a plurality of support locations, and rate adaptation is implemented on the basis of changes in that integral value; see for example, DE 196 09 382 A1 incorporated herein by reference.

In still yet another embodiment, the characteristic which determines the dependency of the stimulation rate on the impedance value, as the first essential operating parameter of the rate-determining apparatus, is not static but is optimized continuously or at given time intervals on the basis of the detection of the AV-time in the event of a modulated stimulation rate. In such an embodiment, the width of variation and particularly the ICLR, as a second essential parameter, is not known at the beginning of operation. Instead, at the beginning of such an operation, an estimated value is predetermined as a starting value for the upper and lower limit values of the width of variation, and this value is continuously optimized during operation.

BRIEF DESCRIPTION OF THE FIGURE

Advantageous developments of the invention are moreover characterised in the appendant claims or are set forth in greater detail hereinafter together with the description of a preferred embodiment of the invention with reference to FIG. 1, wherein:

DETAILED DESCRIPTION OF THE INVENTION

Figure 1:
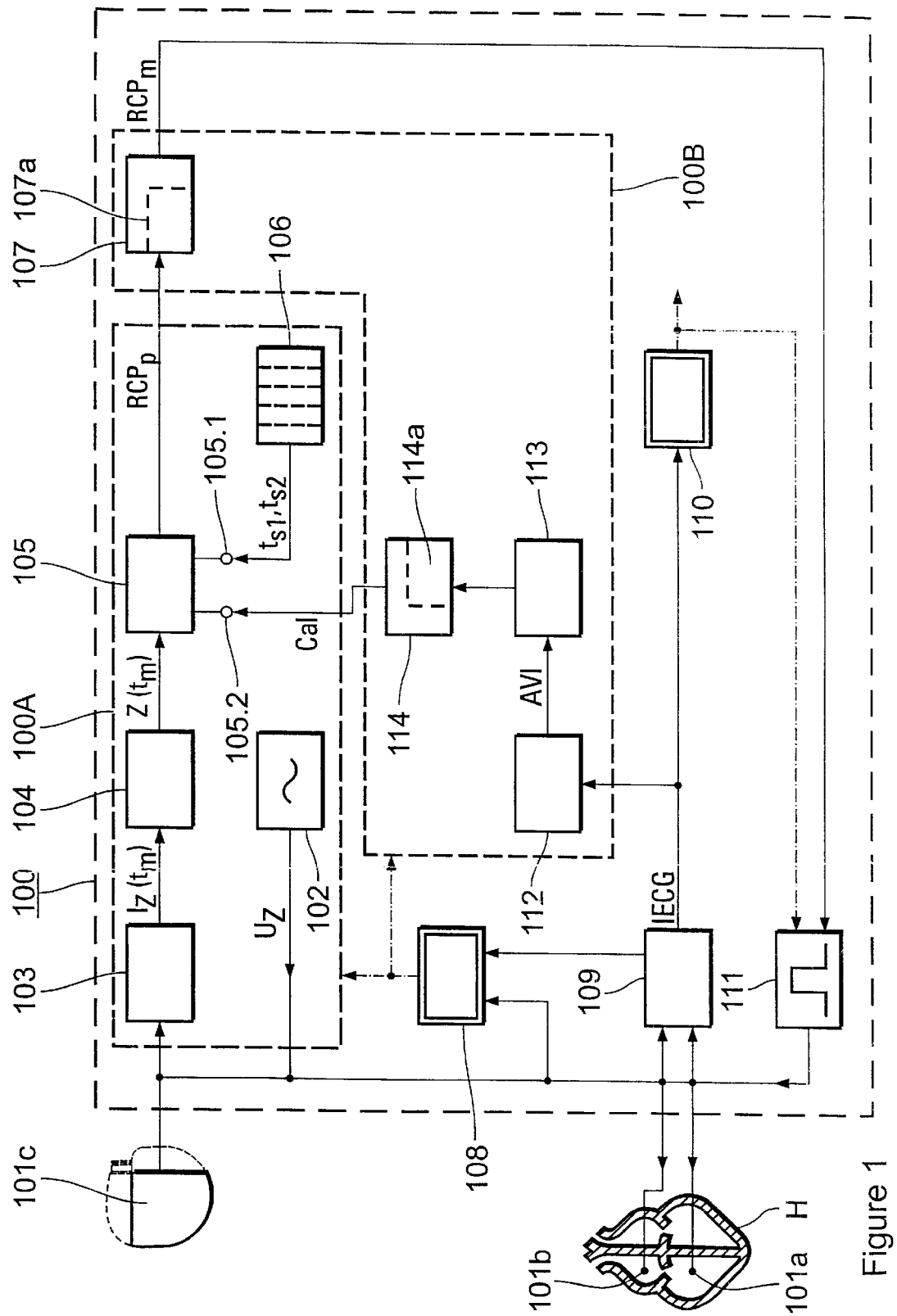
FIG. 1 is a functionary block circuit diagram of a cardiac pacemaker according to the present invention.

The present invention is directed to a self-calibrating rate-adaptive cardiac pacemaker, and more particularly to a self-calibrating rate-adaptive cardiac pacemaker comprising a first measuring and processing device for detecting a first, predominantly sympathetically influenced physiological parameter (Z(tm)) and for obtaining a rate control parameter (RCPp), which has a control input for controlling the functional dependency of the rate control parameter on the first physiological parameter, in particular a response factor and/or an upper limit rate; and a stimulator unit for producing and outputting stimulation pulses at a stimulation rate which is determined by the rate control parameter, characterized by a second measuring and processing device for detecting and evaluating a second, predominantly vagally influenced physiological parameter (AVI) and for outputting a calibration signal (Cal) which is dependent on the evaluation result, to the control input of the first measuring and processing device.

FIG. 1 shows a fragmentary functional block circuit diagram of an embodiment of the invention in the form of a rate-adaptive cardiac pacemaker 100. The block circuit diagram depicts only those components which are important in terms of describing the invention.

Connected to the cardiac pacemaker 100 in the right ventricle of the heart H are a unipolar pacemaker and a measuring electrode 101a for cardiac signal detection, for measurement of the right-ventricle intra-cardial impedance Z, and as a stimulation electrode; and an atrial sensing and stimulation electrode 101b. A pacemaker housing electrode 101c is provided to serve as a counter-electrode.

Impedance measurement is effected in any conventional manner by a procedure whereby the electrode 101a is supplied with a measuring voltage Uz by a measuring voltage generator 102, and the current Iz ($t_{in}$) between the measuring electrode 101a and the counter-electrode 101b is then measured by way of a current measuring circuit 103 at a number (m) of equidistantly pre-programmed times $t_{in}$. The values Z(tm) which characterize the variation in time of the impedance are produced at the output of an impedance calculating stage 104 connected on the output side of the current measuring circuit 103, as a quotient from the (fixedly pre-set) measuring voltage and the measured current values. In an RCP-calculation stage 105, which is connected by way of a first control input 105.1 to a sensing time memory 106 and which receives a response factor control signal by way of a second control input 105.2, a primary rate control parameter value RCPp is calculated for each detected impedance time variation Z(tm).

In a modulator stage 107, connected on the output side of the RCP-calculation stage 105, a predetermined modulation pattern, which is stored in a pattern memory 107a, is impressed on the primary RCP-values within the relatively short period duration of the cardiac cycle. At each stimulation time, an RCP-value (RCPm), which is varied in accordance with the modulation pattern ('modulated'), is available at the output of the modulator stage 107.

The above-described components 102 through 106 form an impedance processing apparatus 100A of the pacemaker 100, with which the sympathetic nerve component is brought into effect in CLS. A rate adaptation time controller 108 controls both the above-outlined impedance detection and evaluation procedure in the stage 100A and the 'rapid' modulation of the rate control signal in the stage 107, as well as the procedure described hereinafter for detecting and evaluating the AV-transition time (AVI).

Impedance measurement and AVI-detection are triggered by the procedural control system in synchronous relationship with cardiac activity or pacemaker stimulation. For this purpose, the pacemaker, in a conventional manner includes an IECG-input stage 109 (which in practice can be formed by separate atrium and ventricle input stages), a pacemaker operational control 110 and an output stage 111 (which similarly to the input stage can include separate atrium and ventricle stages) as well as additional conventional components. The general function of these components is assumed to be known herein.

With regard to the calibration operation described herein, it should be noted that the pacemaker either operates in the vestibule stimulation mode, such that the impedance is evaluated at the natural ventricular event; or operating mode change-over operations are to be implemented during calibration in order to be able to effect the evaluation of the impedance at the VER and to have the natural AV-interval available. Hereinafter, the pacemaker is assumed to operate in the vestibule stimulation mode.

The IECG-input stage 109 has an AVI-detection stage 112 connected at its output. The output thereof is taken to an AVI-trend-ascertaining stage 113, which includes an AVI-memory 113a for storing a predetermined number of past-AVI-values (at least the penultimate value) and which determines whether (and possibly in what expression) there is a trend for increasing or reducing the length of the AVI in relation to the preceding cardiac cycle or the preceding cycles. Connected to the outputs of the AVI-trend-ascertaining stage 113 and the modulator stage 107 is a calibration signal generator 114 in which the result of AVI-trend ascertainment is correlated with the underlying modulation procedure and, on the basis of a decision matrix stored in an internal memory 114a, a correction or verification signal is determined as a response factor control signal Cal and transmitted to the control input 105.2 of the RCP-calculation stage 105. In the embodiment diagrammatically illustrated in FIG. 1, an outputted control signal is effective for calibration directly for the next cardiac cycle. However, it is also possible to implement correction (or verification) of the response factor in each case only after conclusion of a modulation cycle or even a plurality of cycles and for that purpose to provide means (not shown) for intermediate storage or for time averaging of the response factor control signal.

In the simplest case the decision matrix is a 2×2-matrix in which the options of upwardly or downwardly modulated rates (RCPm>RCPp and RCPm>RCPp respectively) are linked to the consequence of increased-length or reduced-length AV-time (AVI↑ and AVI↓ respectively) by way of four control signal fields which contain one of the response factor control signals 'increase' (RF↑"), 'reduce' (RF↓) or 'maintain' (RF→) according to table 1, below.

TABLE 1

| | Decision Matrix | |
|---|---|---|
| AVI \| Mod. | $RCP_m > RCP_p$ | $RCP_m < RCP_p$ |
| AVI ↑ | RF ↓ | RF → |
| AVI ↓ | RF → | RF |

The above matrix takes into account the fact that the AV-time is reduced in length with a physiologically appropriate rising rate or is increased in length with a falling rate, while 'unphysiological' changes in rate provoke precisely the opposite behavior in terms of the AVI. By taking into account the case involving steady AV-time and differentiation in accordance with the magnitude of the respective changes in a suitably enlarged matrix, it is possible to derive a refined calibration algorithm which responds even more rapidly. It is to be noted that the MCLR can also be calibrated by means of the above-described matrix or a similar matrix. In such a case, besides the response factor and more specifically, in the event of a high stress on the patient—as in any other stress condition—the increase in length of the AVI, which indicates an unphysiological rate increase, will trigger a reduction in the response factor until there is no longer any increase worth mentioning in the stimulation rate. This system affords an effective upper rate limitation effect.

The units 107 and 112 through 114 form the calibration stage 100B of the pacemaker, with which the vagus nerve component or the parasympathetic influence in CLS is brought into effect.

The signal connection of the pacemaker control 110 to the intracardial electrodes 101a, 101b, with which cardiac actions or intracardial ECGs are recorded, also makes it possible to draw a distinction between spontaneous and evoked cardiac actions and thus makes it possible to take into account the type of event with regard to the impedance-based rate calculation.

In particular, at each change in event type it is possible by means of the pacemaker control to add to the calculated stimulation rate a value from a plurality of internally stored rate offset values. In such a case, the magnitude of the added value is selected in dependence on the preceding and the current RCP-values such that the jump in rate does not exceed a predetermined amount, and which is returned to zero in a stepwise manner in the case of the cardiac events which then follow. The specific circuitry means for implementing this additional function are available to the man skilled in the art from conventional arrangements for smoothing jump functions of control parameters and more specifically for rate configuration smoothing in pacemakers.

Instead of the above-mentioned sensors, it is also possible to use other sympathetically or vagally dominated sensors. It is additionally possible to provide a position sensor whose signals, by way of a suitable algorithm, influence processing of the impedance signal to allow the system to take into account the orthostasis effect.

In a further modified embodiment, besides the two closed-loop sensors, there is additionally provided an activity sensor or another 'non-closed-loop' sensor which can further increase the range of use and the reliability of the calibration algorithm and which can possibly take over rate control if (for example due to faults or disturbances or altered symptoms) auto-calibration of the CLS, in accordance with the programmed algorithm, should not be possible over relatively prolonged periods of time.

The present invention is not limited in its implementation to the preferred embodiments set forth hereinbefore by way of example. On the contrary, it is possible to conceive of a number of variants which make use of the claimed solution, even in a construction of a different kind.

What is claimed is:

1. A self-calibrating rate-adaptive cardiac pacemaker, comprising a first measuring and processing device for detecting a first, predominantly sympathetically influenced physiological parameter and for obtaining and outputting a rate control parameter, the first measuring and processing device having a control input for controlling the functional dependency of the rate control parameter on the first physiological parameter, and a stimulator unit for producing and outputting stimulation pulses at a stimulation rate which is determined by the rate control parameter, the stimulation unit having a second measuring and processing device for detecting and evaluating a second, predominantly vagally influenced physiological parameter and for outputting a calibration signal which is dependent on the evaluation of the predominantly vagally influenced physiological parameter to the control input of the first measuring and processing device.

2. A cardiac pacemaker as set forth in claim 1 wherein the first measuring and processing device is adapted for measuring and processing a parameter which characterizes ventricular cardiac activity, and the second measuring and processing device is adapted for measuring and processing a parameter which characterizes either atrial cardiac activity or a time correlation between atrial and ventricular activity.

3. A cardiac pacemaker as set forth in claim 1 or claim 2 further comprising separation means for separating vagally influenced components in the rate control parameter of the first measuring and processing device and/or sympathetically influenced components in the calibration signal of the second measuring and processing device.

4. A cardiac pacemaker as set forth in claim 3 wherein there is provided a modulation device associated with said separation means, for producing a modulated rate control signal with a modulation rate corresponding to the typical time constant of sympathetically or vagally controlled activity, and a trend determination device for evaluating the influence of the modulation on the respective calibration signal.

5. A cardiac pacemaker as set forth in claim 4 wherein the modulation device for producing a modulated rate control signal for evaluating the influence on the calibration signal of the second measuring and processing device implements modulation with a time constant which approximately corresponds to either a cardiac cycle or stimulation interval.

6. A cardiac pacemaker as set forth in claim 2 wherein the first measuring and processing device is in the form of an impedance measuring and processing device for detecting the right-ventricle impedance and for determining either the rise or the integral of the impedance-time function in a predetermined sensing time interval.

7. A cardiac pacemaker as set forth in claim 2 wherein the second measuring and processing device is adapted for detecting and evaluating a natural AV-transition time.

8. A cardiac pacemaker as set forth in claim 1 further comprises an additional body sensor which is not responsive to a signal from the heart-circulation regulating circuit.

9. A cardiac pacemaker as set forth in claim 1 wherein the first physiological parameter is either a response factor and/or an upper limit rate.

10. A cardiac pacemaker as set forth in claim 8 wherein the heart-circulation regulating circuit is either an activity or an orthostasis sensor.

* * * * *

UNITED STATES PATENT AND TRADEMARK OFFICE
CERTIFICATE OF CORRECTION

PATENT NO.    : 6,463,325 B1
DATED         : October 8, 2002
INVENTOR(S)   : Armin Bolz It is certified that error appears in the above-identified patent and that said Letters Patent is hereby corrected as shown below:

<u>Title page,</u>
Item [73], Assignee, change to -- Biotronik Mess-und Therapiegerate GmbH & Co. Ingenieurburo Berlin --.

Signed and Sealed this

Seventeenth Day of February, 2004

JON W. DUDAS
*Acting Director of the United States Patent and Trademark Office*